(12) United States Patent
Millar

(10) Patent No.: US 6,994,695 B1
(45) Date of Patent: Feb. 7, 2006

(54) PRESSURE SENSING MODULE FOR A CATHETER PRESSURE TRANSDUCER

(75) Inventor: Huntly D. Millar, Houston, TX (US)

(73) Assignee: Millar Instruments, Inc., Houston, TX (US)

( * ) Notice: Subject to any disclaimer, the term of this patent is extended or adjusted under 35 U.S.C. 154(b) by 600 days.

(21) Appl. No.: 10/127,154

(22) Filed: Apr. 19, 2002

Related U.S. Application Data

(63) Continuation of application No. 09/435,502, filed on Nov. 6, 1999, now Pat. No. 6,394,986.

(51) Int. Cl.
*A61M 25/00* (2006.01)

(52) U.S. Cl. .................................. 604/264; 600/488
(58) Field of Classification Search .............. 600/488, 600/486; 604/561, 264; 73/706, 708, 721, 73/726–727
See application file for complete search history.

(56) References Cited

U.S. PATENT DOCUMENTS

| | | | |
|---|---|---|---|
| 3,277,718 A | 10/1966 | Ruge | |
| 3,315,201 A | 4/1967 | Werne | |
| 3,417,360 A | 12/1968 | Heller et al. | |
| 3,480,003 A | 11/1969 | Crites | |
| 3,550,583 A | 12/1970 | Chiku et al. | |
| 3,553,625 A | 1/1971 | Stedman | |
| 3,710,781 A | 1/1973 | Hutchins, IV et al. | |
| 3,748,623 A * | 7/1973 | Millar | 338/4 |
| 3,831,588 A * | 8/1974 | Rindner | 600/488 |
| 3,946,724 A | 3/1976 | La Balme | |
| 4,023,562 A | 5/1977 | Hynecek et al. | |
| 4,191,193 A * | 3/1980 | Seo | 600/488 |
| 4,274,423 A * | 6/1981 | Mizuno et al. | 600/488 |
| 4,665,925 A | 5/1987 | Millar | |
| 4,722,348 A | 2/1988 | Ligtenberg et al. | |
| 4,771,782 A | 9/1988 | Millar | |
| 4,878,898 A | 11/1989 | Griffin et al. | |
| 4,881,410 A * | 11/1989 | Wise et al. | 73/724 |
| 4,941,473 A | 7/1990 | Tenerz et al. | |
| 5,207,103 A | 5/1993 | Wise et al. | |
| 5,257,630 A * | 11/1993 | Broitman et al. | 600/488 |
| 5,306,252 A | 4/1994 | Yutori et al. | |
| 5,348,481 A | 9/1994 | Ortiz | |

(Continued)

FOREIGN PATENT DOCUMENTS

WO          88/00810          2/1988

OTHER PUBLICATIONS

*Cardiac Catheterization and Angioplasty*, 3rd Ed., Lea and Febiger, pp. 493-501.

(Continued)

*Primary Examiner*—Manuel Mendez
(74) *Attorney, Agent, or Firm*—Charles D. Huston; Daffer McDaniel, LLP

(57) ABSTRACT

The present invention relates to a pressure sensor module for use in catheters having a pressure sensor operable to provide a signal representative of pressure. The pressure sensor includes a sensing side and a pressure reference side. At least one signal transmission media is coupled to the sensor for transmitting the signal representative of pressure. A convex-shaped carrier is provided having a slot formed to expose the sensing side of the sensor. The convex-shaped carrier is adapted for receiving the sensor such that the sensing side of the sensor is adjacent the slot. A bonding material is provided for mounting the sensor to the carrier. The pressure sensing module provides ease of installation and manufacture because the module may easily be bonded and installed within a catheter.

18 Claims, 5 Drawing Sheets

U.S. PATENT DOCUMENTS

| | | | |
|---|---|---|---|
| 5,352,223 | A | 10/1994 | McBrayer et al. |
| 5,415,178 | A | 5/1995 | Hsi et al. |
| 5,431,628 | A | 7/1995 | Millar |
| 5,564,434 | A | 10/1996 | Halperin et al. |
| 5,688,267 | A | 11/1997 | Panescu et al. |
| 5,715,827 | A | 2/1998 | Corl et al. |
| 5,993,395 | A | 11/1999 | Shulze |
| 6,213,943 | B1 | 4/2001 | Abreu |
| 6,221,024 | B1 * | 4/2001 | Miesel .................. 600/486 |
| 6,272,371 | B1 * | 8/2001 | Shlomo ................. 600/424 |
| 6,699,186 | B1 * | 3/2004 | Wolinsky et al. ........ 600/300 |

OTHER PUBLICATIONS

Aroesty, "Pertcutaneous intra-aortic balloon insertion," *Cardiac Catheterization and Angiography*, Lea & Febiger, 3rd Ed., pp. 493-505, 1986.

Arrow Instructions for use: sheathed intra-aortic balloon catheter insertion for NarrowFlex™ IAB's.

Brochure entitled "Millar Instruments, Inc. Mikro-Tip Catheter Transducers," 1994.

Geddes, "Direct Measurement of Blood Pressure," *The Direct and Indirect Measurement of Blood Pressure*, Yr. Book Med. Publ., Inc., 1970, pp. 33-34.

Marieb, "Fetal circulation diagram," *Essentials of Human Anatomy & Physiology*, Benjamin/Cummings Publication Co., Inc., 4th Ed., p. 327, 1994.

Marieb, "Major arteries diagram," *Essentials of Human Anatomy & Physiology*, Benjamin/Cummings Publication Co., Inc., 4th Ed., p. 321, 1994.

McDermott et al., "Monitoring Acute Compartment Pressures with S.T.I.C. Catheter," Clinical Orthopaedics and Related Research, 190, 192-198, 1984.

Robert A. Jeanmenne Jr., et al., "Electroless Plating on Medical Catheters," from the Internet at http://www.gardnerweb.com/pf/magazine/articles/089704a.htm.

Sherwood, Human Physiology, Cardiac cycle diagram, p. 279, 1989.

Sherwood, Human Physiology, Heart valve diagram, p. 265, 1989.

Sherwood, Human Physiology, Blood flow diagram, p. 261, 1989.

* cited by examiner

PRESSURE SENSING MODULE FOR A CATHETER PRESSURE TRANSDUCER

RELATED APPLICATIONS

This application is a continuation application of U.S. application Ser. No. 09/435,502 entitled "Pressure Sensing Module for a Catheter Pressure Transducer" filed Nov. 6, 1999, now U.S. Pat. No. 6,394,986 which is hereby incorporated herein by reference. The benefit of 35 U.S.C. § 120 is claimed for the above referenced application.

BACKGROUND OF THE INVENTION

1. Field of the Invention

The present invention relates to a pressure sensing module for use in catheters. More specifically, the present invention relates to a pressure sensing module that lends itself to easy installation and replacement, and provides a very low profile device for installation in a catheter.

2. Related Art

Catheter pressure transducers are long slender flexible tubular catheters with one or more pressure sensors mounted along the length of the catheter. These devices are used for making direct pressure measurements at various locations within a human or animal body by insertion through body orifices or through surgical incisions. The catheter pressure transducer may also be inserted through other catheters previously positioned within the body. These catheters include high fidelity pressure sensors for measuring pressure and pressure gradients. For example, catheter pressure transducers may be used in the various chambers of the heart and throughout the cardiovascular system. These catheters have also been used for measuring peristaltic activity in the intestines, pressure gradients in the urinary tract, rectal pressures, esophageal pressures, and intracranial pressures.

Present catheter pressure sensors typically take the form of photoelectric-type sensors, resistive-type sensors, or capacitive-type sensors. In the case of photoelectric-type transducers, light fibers pass the pressure signals from the sensor through the length of the catheter to a measurement device. Similarly, resistive-type and capacitive-type sensors use insulated electrical wires to pass pressure signals from the sensor through the catheter.

Exemplary sensors include small strain gauge-type pressure sensors that are made from a semiconductor material such as silicon. These semiconductor devices are generally shaped like a brick from which has been machined or etched a hollowed out region behind a diaphragm with diffused strain gauges for sensing the degree of diaphragm distortion under applied pressure. The sensors further include circuitry for providing electrical signals representative of the pressure sensed by the strain gauge to pads that may be connected to external devices. In operation, one side of the strain gauge diaphragm is equalized to a reference pressure, such as atmospheric pressure (the reference side), and the other side of the strain gauge diaphragm is exposed to the body tissues or fluids (sensing side). Such semiconductor strain gauge pressure sensors provide high-fidelity pressure measurements.

Traditionally, to mount the sensor within the catheter, a cavity is molded within the catheter or a premolded carrier is placed within the catheter to accept the sensor. When mounting the sensor, it is important to isolate the pressure sensor from mechanical movement and mechanical stresses that might sufficiently deform the sensor to give false pressure readings. The primary prior technique for mounting a semiconductor pressure sensor to a catheter has been to use a tubular metal casing, such as a portion of a stainless steel hypodermic needle. With this sturdy metal casing surrounding the sensor, the sensor is isolated from catheter movement and is sensitive only to external pressure. The proximal end of the metal casing is connected to the catheter body and is open to allow electrical connections from the catheter to reach the semiconductor pressure sensor. The proximal end is also open to allow venting of the back of the reference side of the strain gauge diaphragm to an external pressure through a lumen in the catheter body. With such prior devices, a window is generally cut into the side of the tubular metal casing. The sensing side of the strain gauge diaphragm of the sensor is left exposed through the window to applied external pressures from body fluids and tissues.

After mounting the sensor within the catheter, the wires from the sensor are bonded, either with a conductive epoxy or by soldering, to wires that have already been prepared within the catheter by an appropriate scraping or pretinning procedure. Wires within the catheter are typically 0.003" in diameter, with wires from the sensor being typically approximately 0.001" in diameter. These are all delicate wires to handle and to bond together. The sensor is usually attached in place with an epoxy resin or with a flexible RTV (room temperature vulcanizing silicone rubber).

When the mounting material has cured, a cleaning process is generally required to remove any flux or materials used in bonding the wires. Then, the wire connections are generally coated with an RTV or epoxy resin and the gap on the edges of the sensor between the sensor and the housing are generally sealed with an RTV. After these materials have been cured, an additional layer of epoxy and/or RTV is added to provide a smooth contour for the sensor area that will be compatible with the requirements for introduction into body vessels.

All these procedures are delicate and time-consuming and require skill, patience, and time to accomplish successfully. Because it is often difficult to apply an absolutely uniform coating of RTV, as required for consistency in pressure measurement, the results of the installation of the new sensor are not always what is required and the RTV may have to be modified or the sensor replaced again to meet stability requirements essential for good performance of a catheter pressure sensor. In addition, these installation procedures are typically performed directly within the catheter. This work is extremely delicate, time-consuming, and expensive.

In addition, prior catheter pressure transducers are either for single use, as sterile disposable items, or for multiple uses, wherein they will be cleaned and sterilized and reused for dozens and perhaps hundreds of times. Because the catheters are often very small in diameter (e.g., 0.5 mm to 3 mm), as for example when introduced into small vessels in the cardiovascular system, the pressure sensors are somewhat delicate devices and can be damaged during use.

Therefore a need exists for a device that lends itself to be easily installed during manufacture of the catheter and to be easily replaced as required. Further, a need exists for a pressure sensor that minimizes the problems and reduces the costs associated with traditional manufacturing procedures.

SUMMARY OF THE INVENTION

The present invention achieves these goals with a unique and advantageous structure for a pressure sensing module that may be used in the construction of reliable catheter pressure transducers. The pressure sensing module provides ease of installation and manufacture. In particular, the present invention reduces manufacturing costs by allowing most of the delicate work associated with building a catheter pressure transducer to be performed ahead of time on a separate module. Multiple modules may be built simultaneously without having to modify one catheter at a time.

The present invention also provides unique advantages relating to the modularity of the pressure sensing module. The pressure sensing module of the present invention is a self-contained rigid structure that may be easily installed and bonded to a catheter. In addition, the pressure sensing module may be readily removed and replaced.

The pressure sensing module of the present invention is a low profile device that allows for a larger opening within a catheter. The larger opening within the catheter allows for more electrodes or wires to run to the sensor. Additionally, the larger vent provides more room within the catheter for the insertion of other devices such as a guidewire.

In an embodiment, the present invention is a pressure sensor module for use in catheters having a pressure sensor operable to provide a signal representative of pressure having a sensing side and a pressure reference side. At least one signal transmission media is coupled to the sensor for transmitting the signal representative of pressure. A convex-shaped carrier is provided having a slot formed to expose the sensing side of the sensor. The convex-shaped carrier is adapted for receiving the sensor such that the sensing side of the sensor is adjacent the slot. A bonding material is provided for mounting the sensor to the carrier.

In alternate embodiments, the pressure sensor module includes a resistive-type sensor. Other sensors may be used including capacitive-type, sensors or photoelectric-type sensors.

In yet another embodiment, the bonding material for mounting the sensor to the carrier is flexible RTV. The bonding material may also be epoxy resin.

In another aspect of the present invention, a catheter pressure transducer is provided having a catheter body with an internal lumen providing access to an external reference pressure. A tube with an open channel is inserted within and extending along at least a portion of the internal lumen of the catheter. The tube is slot-cut to form a slotted sleeve along a portion of the tube. A first signal transmission media extends along the internal lumen of the catheter. A convex-shaped pressure sensor module having a pressure sensor operable to provide a signal representative of pressure is provided wherein the convex-shaped pressure sensor is coupled to the slotted sleeve of the tube such that the convex-shaped pressure sensor is approximately the same size as the catheter body. A second signal transmission media is coupled to the sensor for transmitting the signal representative of pressure. The second signal transmission media is bonded to the first transmission media in order to transmit the signal representative of pressure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1A:
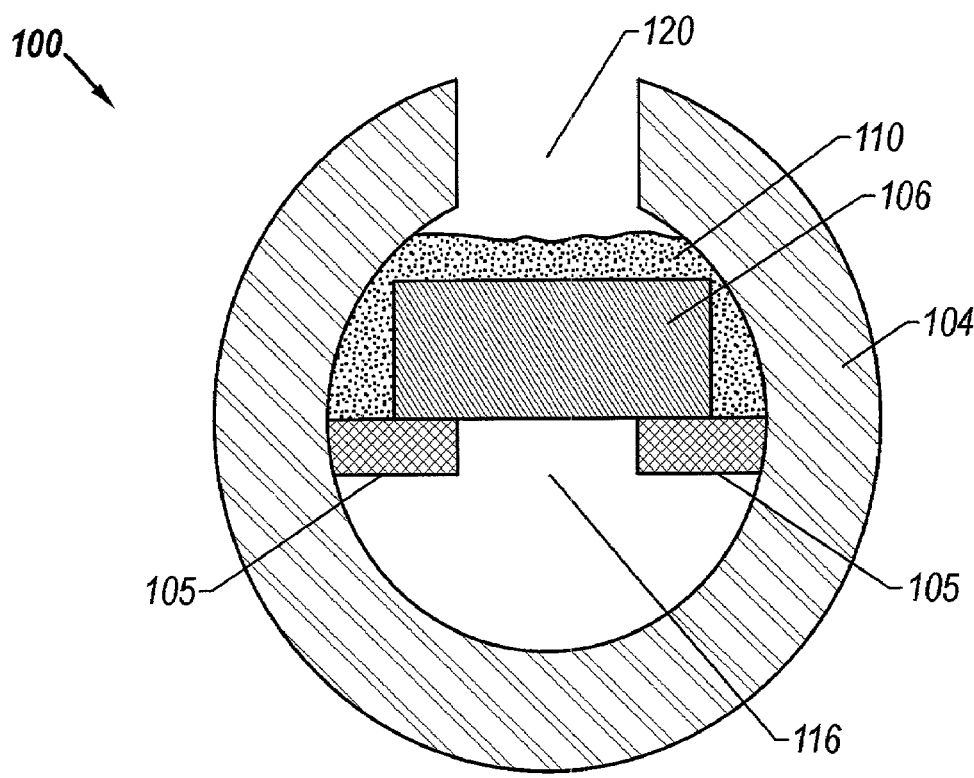
FIG. 1A (prior art) is an end cross-section view of a prior art catheter pressure transducer.
Figure 1B:
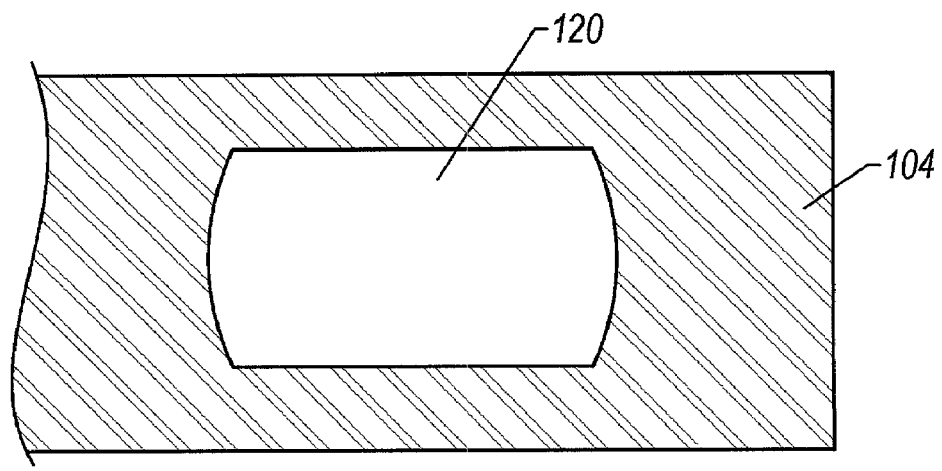
FIG. 1B (prior art) is a top view of a casing for a prior art catheter pressure transducer.

An example of a prior catheter tip pressure transducer device is shown with reference to FIG. 1A (prior art) and FIG. 1B (prior art), which collectively depict the general structure of a prior device 100. FIG. 1A (prior art) depicts an end cross-section view of a tubular metal casing 104 of a prior catheter tip measurement device 100 in the area that the semiconductor pressure sensor 106 is located. FIG. 1B (prior art) depicts a top view of the metal casing 104 showing a window 120 that exposes the sensing side of the diaphragm on the semiconductor pressure sensor 106 to external pressures.

As mentioned above, a window 120 was generally cut out of tubular metal casing 104. Sensor supports 105 were generally attached to the internal walls of tubular metal casing 104. Once semiconductor pressure sensor 106 was placed inside the tubular metal casing 104 on top of sensor supports 105, a protective material 110 was generally applied to keep body tissues and fluids from contacting the semiconductor pressure sensor 106. Such contact could cause electric shock to the surrounding tissues or damage the pressure sensor. One material that was used as the protective material 110 is flexible room-temperature-vulcanizing (RTV) silicone rubber. This protective material 110 was generally applied over the pressure sensor to a thickness of about 0.002 inch.

The present invention provides a catheter pressure transducer that is less expensive and easier to install and maintain. The present invention comprises a pressure sensing module that allows a pressure sensor to be installed and mounted without having to install a sensor directly into a catheter. Instead, the pressure sensor is installed into a pressure sensing module, which is subsequently attached to a catheter. As used herein, the term "module" means a detachable section, compartment, or unit with a specific purpose or function.

Figure 2A:
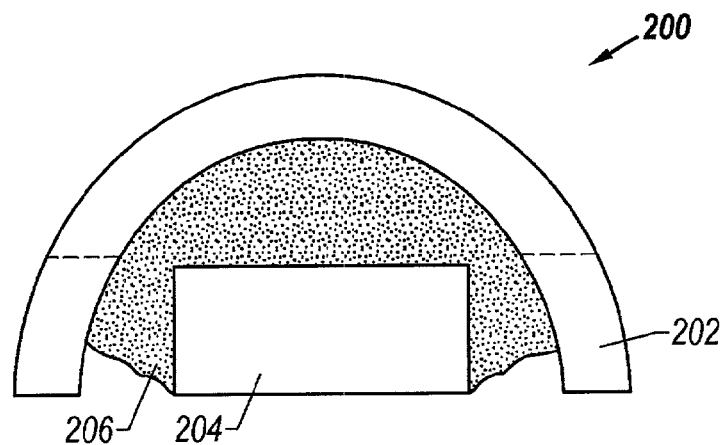
FIG. 2A is an end cross-section view of a pressure sensing module according to the present invention.
Figure 2B:
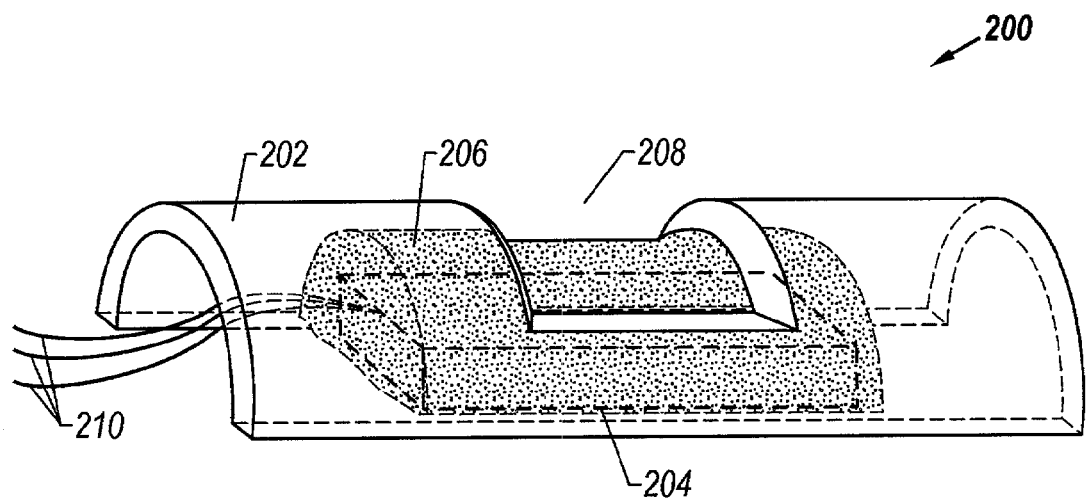
FIG. 2B is a side view of a pressure sensing module according to the present invention.
Figure 2C:
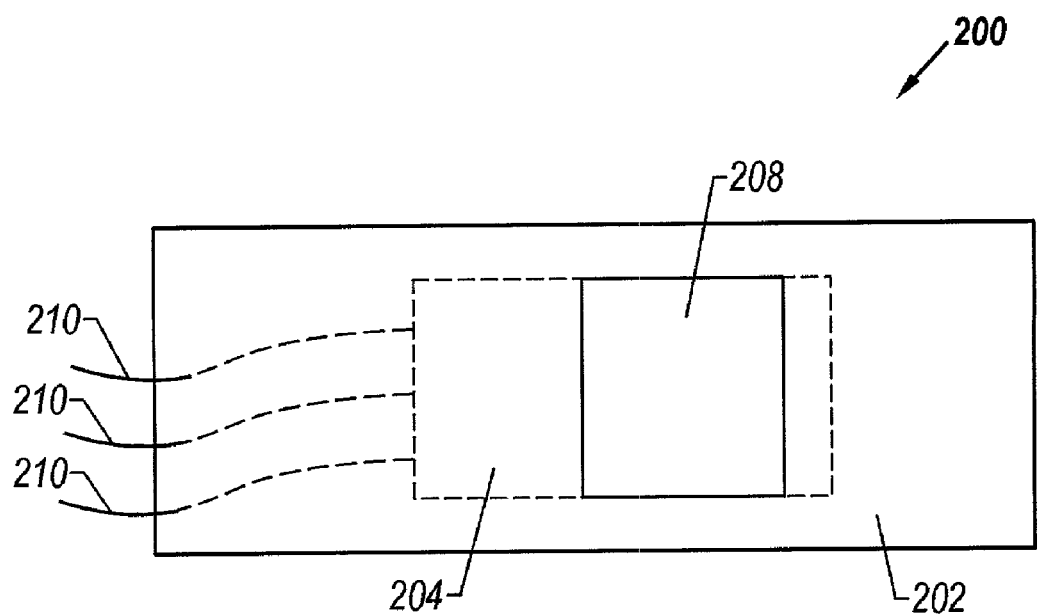
FIG. 2C is a top view of a pressure sensing module according to the present invention.
Figure 2D:
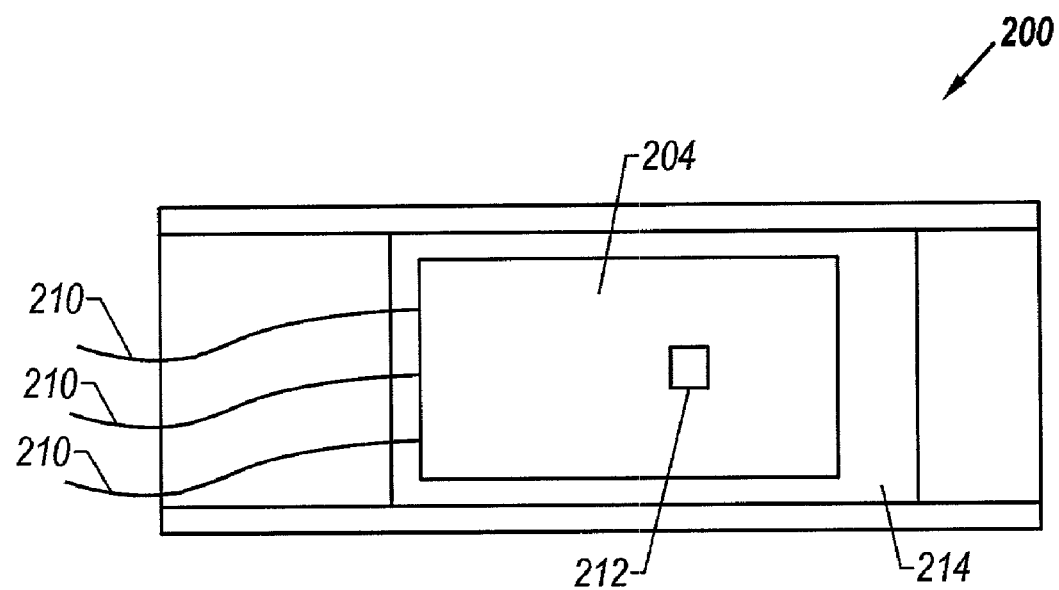
FIG. 2D is a bottom view of a pressure sensing module according to the present invention.
Figure 3:
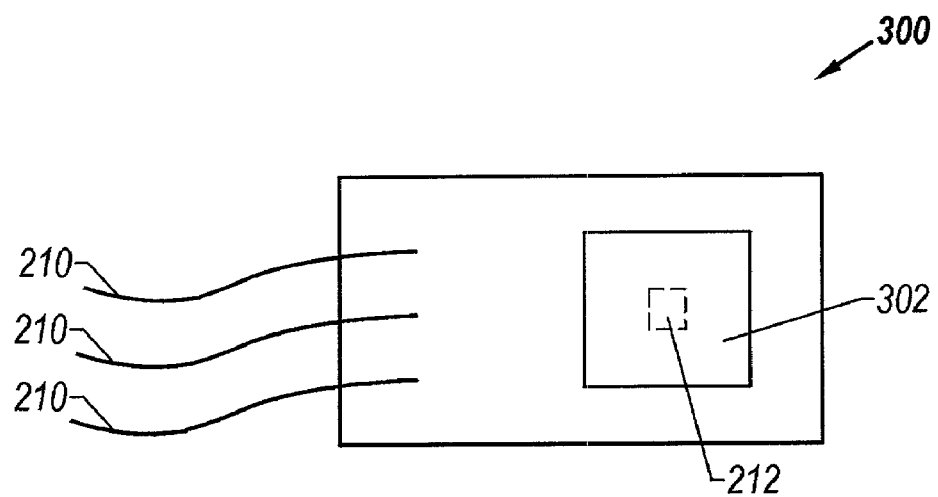
FIG. 3 is a top view of a pressure sensor used in a pressure sensing module according to the present invention.
Figure 4:
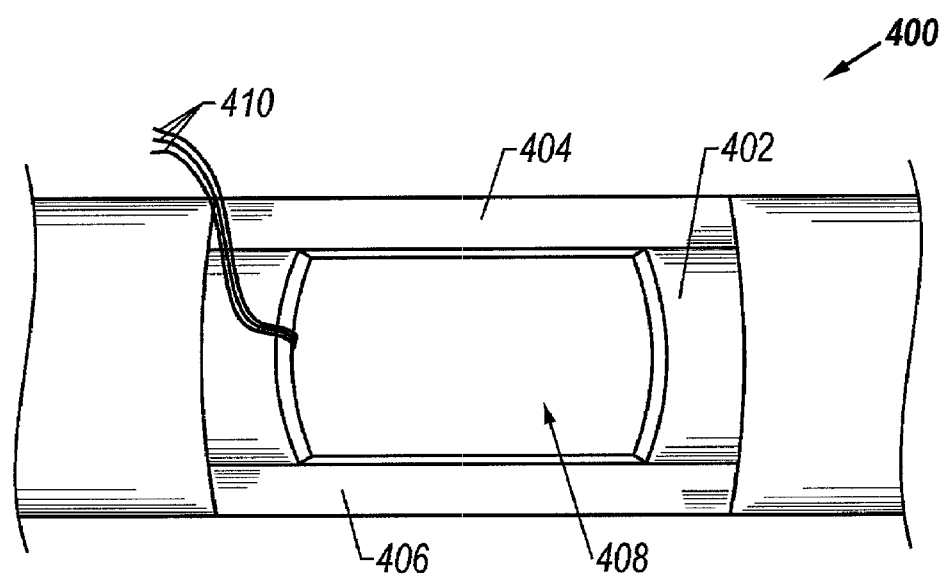
FIG. 4 is a top view of a catheter modified to allow coupling to a pressure sensing module according to the present invention.
Figure 5:
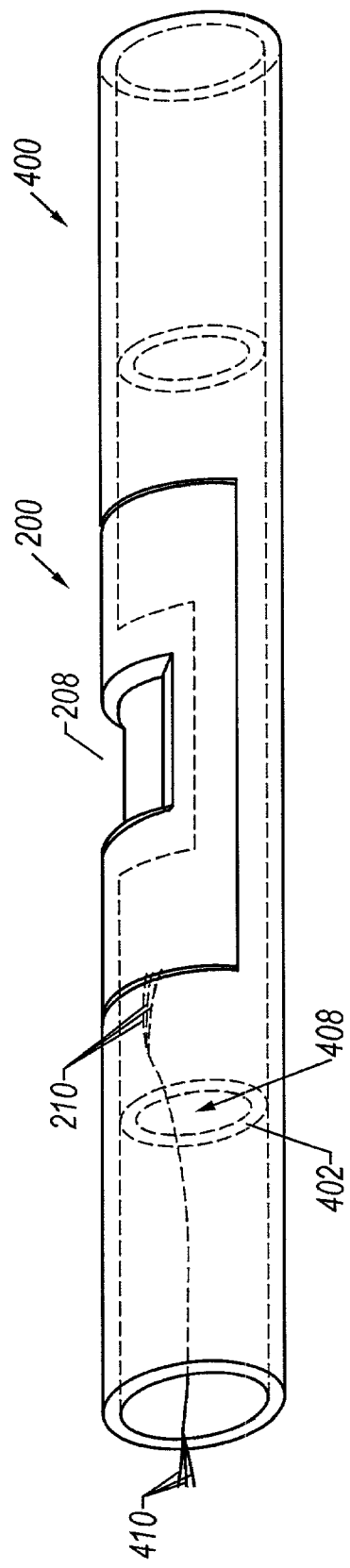
FIG. 5 is a side cross-section view of a catheter pressure transducer with a pressure sensing module according to the present invention.

The present invention may further be understood with reference to the embodiments shown in FIGS. 2A–D, 3, 4, and 5. FIGS. 2A–D depict different views of exemplary pressure sensing module 200 according to the present invention. FIG. 3 provides a top view of a sensor as used in a pressure sensing module according to the present invention. FIG. 4 illustrates a catheter that has been machined to receive an exemplary pressure sensing module according to the present invention. Finally, FIG. 5 depicts the combination of a pressure sensing module and a catheter according to the present invention.

Referring to FIGS. 2A and 2B, a pressure sensing module 200 includes a carrier 202 and a semiconductor pressure sensor 204. The semiconductor pressure sensor 204 is coupled to the carrier 202 using bonding material 206. The carrier 202 is made of stainless steel, a ceramic member, or other suitable material. In an embodiment of the claimed invention, the carrier 202 is constructed in a curved shape to fit the profile of a catheter. The carrier 202, when installed, fits the profile of a catheter and provides an extremely smooth pressure sensing area on the side of the catheter. On the outer convex side of this carrier 202, a slot 208 is machined out by laser cutting, mechanical grinding, chemical etching, or other suitable method for machining the catheter so as to provide an open area corresponding to the size of the diaphragm of the pressure sensor. An exemplary diaphragm may range from 0.25 mm square to 0.5 mm square, although any suitable diaphragm may be used without departing from the scope and spirit of the present invention.

Then, on the inner concave side of the carrier 202, a pressure sensor 204 is attached in such a way that the diaphragm area (sensing side) of the pressure sensor 204 is immediately adjacent the carrier's opening slot 208; the sensor is spaced perhaps 0.001" within the carrier 202 such that there is suitable electrical insulation between the sensor 204 and the carrier 202. The sensor 204 may be attached to the carrier by suitable bonding material, such as a flexible RTV. Wires 210 are pre-attached to the sensor 204 and extend within the convex portion of the carrier 202 to be suitable attached to wires within a catheter.

In the illustrated embodiment, sensor 204 is a resistive-type or capacitive-type sensor. Alternatively, other suitable sensors may be used without departing from the spirit and scope of the claimed invention. For example, sensor 204 may be a photoelectric-type sensor that uses fiber optic connections between the sensor and a measurement device.

FIG. 2C illustrates a top view of a pressure sensing module 200 according to an embodiment of the present invention. As illustrated, a pressure sensor 204 is attached in such a way that the diaphragm area is immediately adjacent the carrier's opening slot 208. To insulate the pressure sensor 204, a flexible insulating material may be applied on top of the pressure sensor 204. In an embodiment, this material is flexible RTV silicone rubber. RTV silicone is slightly tacky and provides good insulating characteristics such that it may be used as the flexible insulating material. It acts as a good sealant and a good insulator without appreciably affecting the pressure signal transmitted to the diaphragm of the pressure sensor. To insulate the system from body tissues, an insulating layer is applied to surround the measuring tip of the device. This insulating layer provides a thin outer sheath that isolates and insulates the electrical measurement components with a drastically reduced feature size than that capable in prior catheter pressures transducers. The insulating layer may be achieved using a thin material that has high dielectric insulating characteristics. In particular, the insulating layer may be made using a polyimide sheath or sleeve. Polyimide is a transparent, relatively inert, biocompatible insulating material available in a variety of thicknesses down to 0.0005 inch. Such a polyimide material is available as polyimide tubing from MicroLumen in Tampa, Fla.

FIG. 2D shows a bottom view of the processor sensing module 200 of the present invention. As illustrated, a flexible insulating material 214 may be applied to secure the pressure sensor 204. In an embodiment, this material is flexible RTV silicone rubber. It should be understood, however, that other suitable insulating materials may be used without departing from the spirit and scope of the present invention. For example, the pressure sensor 204 may be secured using an epoxy. A sensor vent hole 212 provides access to the inner surface of the diaphragm while maintaining the structural integrity of the sensor.

A more detailed view of a pressure sensor 300 according to the present invention is illustrated in FIG. 3. Pressure sensor 300 includes a pressure sensing thin diaphragm area 302. Once again, a sensor vent hole 212 provides access to the inner surface of the diaphragm.

FIG. 4 illustrates a catheter 400 that has been prepared for use with an embodiment of the pressure sensing module of the present invention. Catheter 400 includes a tube 402, which may be metal or other suitable material. Tube 402 prevents catheter 400 from bending at a location near the pressure sensing module. Prior to installing a pressure sensing module in catheter 400, tube 402 is slot-cut to form a slotted sleeve for mating with the pressure sensing module. The slot-cut further forms an open channel 408 to tube 402. In operation, open channel 408 provides a reference pressure for the reference side of the sensor 204 through sensor vent hole 212 of the pressure sensing module of the present invention. Further, as illustrated in this embodiment, the slot-cut also removes a part of the catheter 400 leaving a portion of the catheter remaining (404 and 406). Finally, catheter 400 includes three wires 410 for connecting to the wires 210 associated with the pressure sensor 204.

FIG. 5 illustrates the attachment between an embodiment of the pressure sensing module 200 of the present invention and an exemplary preformed catheter 400 as shown in FIG. 4. Attachment between the pressure sensing module 200 and the catheter 400 may be made by suitable epoxies or RTV. The outer surface may or may not be coated with an additional epoxy resin, as required. The entire installation can be done rapidly, and it does not require the artistry or delicacy of treatment that was traditionally required for installation of a pressure sensor within a catheter.

In the illustrated embodiment, three wires 210 from the sensor are bonded to three wires 410 in the catheter. In an embodiment, the wires are soldered, folded into the catheter, and then epoxy is added to cover the soldered connections. It should be understood, however, that any suitable method for coupling the wires may be used without departing from the spirit and scope of the present invention. For example, the wires from the sensor may be bonded using a conductive material. Wires within the catheter are typically 0.003" in diameter, with wires from the sensor being typically approximately 0.001" in diameter. These are all delicate wires to handle and to bond together.

After bonding, the wire connections are generally coated with an RTV or epoxy resin and the gap on the edges of the sensor between the catheter and the pressure sensing module are generally sealed with an RTV. After these materials have been cured, an additional layer of epoxy and/or RTV may be added to provide a smooth contour for the sensor area that will be compatible with the requirements for introduction into body vessels.

This pressure sensing module 200 achieves not only a simplicity of installation and replacement, but it also provides a very low profile device for installation in the wall of catheter 400. Once again, the sensor 204 is mounted extremely close to the outer surface of pressure sensing module 200, such that a large open channel 408 is formed. Accordingly, much of the area within the catheter is then free for passage within the catheter 400 of other wires for other pressure sensors or even a lumen for passage of fluids or a guidewire alongside or past the sensing module. With conventional mounting, the sensor is often recessed within the body of the catheter leaving minimal or no room for passage of such lumens or other wires.

Open channel 408 provides a reference pressure to the vent at the reference pressure side of the pressure sensor 204. Although the shape and size of this vent opening is not significant for purposes of providing a reference pressure (an opening of approximately 0.002 inch or more in diameter is generally required to achieve the venting requirement), the size of the venting channel may be important when attempting to include multiple wires through the open channel 408. In an embodiment, a catheter pressure transducer may have a large number of sensors, requiring a number of wires to extend from the sensors up the catheter to measurement devices. For example, a catheter pressure transducer may have four sensors, requiring up to twelve wires to extend from the pressure sensor through the catheter to measurement devices. In other applications, the open channel 408 may be used for insertion of guidewires. By using a pressure sensing module according to the present invention, an open channel on the order of two times the size of prior channels may be achieved over prior catheter pressure transducers.

In conventional catheter pressure transducers, when an area is left open for the mounting of a pressure sensor, the catheter is somewhat weakened at the point of installation and thicker walled and stronger internal structures may be required to reinforce the structure at that point. According to the present invention, when the pressure sensing module 200, particularly if it is made of steel, is installed across the open area in the catheter 400, it is bonded at both ends and tends to reinforce the catheter rather than weaken it. In an exemplary embodiment, the pressure sensing module 200 is bonded to the catheter 400 using epoxy resin. This structure provides an overall stronger catheter and allows for a larger open area to be maintained within the catheter for the passage of wires, lumens, guidewires, etc.

The pressure sensor module 200 further provides benefits due to the reduced size of the opening above the pressure sensor. In certain applications, such as doing measurements of pressures within the lower intestines, catheter pressure sensors are subjected to very corrosive fluids and vapors. Such vapors can diffuse through RTV or silicone rubbers, causing damage and corrosion to the conductive wires used within the catheter. Construction with a pressure sensing module 200 significantly reduces the size of the opening exposed above the pressure sensor 204, since only the diaphragm is exposed, and minimizes the area through which vapors can diffuse to damage wires or structures within the catheter, significantly improving the durability and longevity of such devices.

In addition, sensors that are mounted directly into catheters with a combination of RTV and epoxy resins often show drift characteristics when the catheter is put in water because of minute deformation of the surrounding materials as they absorb humidity. With the pressure sensing module 200, the sensor 204 is attached with RTV to a rigid carrier in a manner that isolates it from any surrounding materials in the catheter 400. Pressure sensing modules 200, by their open structure, can be made identical to one another, with exceptional stability and long term performance characteristics. Because the sensor 204 is contained in the module 200, and not independently bonded to any of the materials in the catheter 400, it is more isolated from the catheter 400 than prior catheter pressure transducers and can therefore give consistently good performance independent of the catheter in which it is mounted.

The pressure sensor module 200 of the present invention provides additional benefits relating to the time and costs associated with manufacturing a catheter pressure transducer. Because the module 200 is manufactured separate from the catheter, many units can be built together in a small working area. Precise locating jigs are required for mounting the sensor on the carrier, but such mounting fixtures can be used again and again, further reducing the cost of the pressure sensing module compared to the one-at-a-time assembly costs of mounting a pressure sensor within a catheter.

In addition, if a sensor becomes broken or requires replacement, the entire carrier 202 with pressure sensor 204 may be easily pried loose or dissected out, the wires 210 unattached, and a new pressure sensing module installed as in the initial installation. Also, in a catheter, there are several periods of time during which the assembly must be put to one side on a temperature-controlled fixture for suitable epoxy and RTV curing. With the pressure sensing module, many units can be assembled at one time and a common curing time for all of them is appropriate. When a typical installation and testing time for installing a pressure sensor in the convention method may be one to two hours, the equivalent time for preparing a sensor module and installing it and testing it may be as little as 30 minutes. The overall cost reduction, not only for the initial installation, but because of the ease of replacement, becomes significant in the assembly of catheter pressure transducers.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as exemplary embodiments. Various changes may be made in the shape, size, and arrangement of parts. For example, equivalent elements or materials may be substitute for those illustrated and described herein, and certain features of the invention may be utilized independently of the use of other features, all as would be apparent to one skilled in the art after having the benefit of this description of the invention.

What is claimed is:

1. A miniaturized pressure sensing module for determining pressure within a living body, said pressure sensing module comprising:
   a sensor operable to provide a signal representative of pressure, said sensor having a sensing side and a pressure reference side;
   at least one signal transmission media coupled to said sensor for transmitting the signal representative of pressure;
   a semicylindrical carrier having a slot, which is formed through a wall of the carrier to expose the sensing side of said sensor to the pressure within the living body, wherein said carrier is adapted for receiving said sensor such that the sensing side of said sensor is adjacent to the slot; and
   bonding material for mounting said sensor to said carrier, such that the sensing side of said sensor is coupled to a concave inner surface of the carrier;
   wherein said miniaturized pressure sensing module is adapted for attachment to a catheter; and
   wherein said miniaturized pressure sensing module is adapted for insertion into said living body.

2. The miniaturized pressure sensing module as claimed in claim 1, wherein said sensor is selected from a group comprising a resistive-type sensor, a capacitive-type sensor, a photoelectric-type sensor, and a strain-gauge-type sensor.

3. The miniaturized pressure sensing module of claim 1, wherein said bonding material is selected from a group comprising flexible RTV silicone rubber and epoxy resin.

4. The miniaturized pressure sensing module of claim 1, wherein said pressure reference side is exposed to atmospheric pressure.

5. The miniaturized pressure sensing module of claim 1, wherein said pressure reference side is exposed to a vacuum.

6. The miniaturized pressure sensor module of claim 1, wherein said sensor is operable to provide a signal that is representative of cardiac pressure.

7. The miniaturized pressure sensor module of claim 1, wherein said sensor is operable to provide a signal that is representative of intracranial pressure.

8. The miniaturized pressure sensor module of claim 1, wherein said sensor is operable to provide a signal that is representative of rectal pressure.

9. The miniaturized pressure sensor module of claim 1, wherein said sensor is operable to provide a signal that is representative of esophageal pressure.

10. The miniaturized pressure sensor module of claim 1, wherein said sensor is operable to provide a signal that is representative of gastrointestinal pressure.

11. The miniaturize pressure sensor module of claim 1, wherein said sensor is operable to provide a signal that is representative of blood pressure.

12. The miniaturized pressure sensor module of claim 1, wherein said sensor is operable to provide a signal that is representative of pressure in a urinary tract of said living body.

13. The miniaturized pressure sensor module of claim 1, wherein the slot is configured for exposing only a portion of the sensing side of said sensor.

14. The miniaturized pressure sensor module of claim 13, wherein a size of the slot is selected from a range comprising about 0.25 mm$^2$ to about 0.5 mm$^2$.

15. The miniaturized pressure sensor module of claim 1, wherein the carrier is formed from a substantially rigid material.

16. The miniaturized pressure sensor module of claim 13, wherein the substantially rigid material is selected from a group comprising metals and ceramics.

17. The miniaturized pressure sensor module of claim 1, wherein the carrier of the miniaturized pressure sensor module is adapted for attachment to the catheter, such that a convex outer surface of the carrier is flush with a convex outer surface of the catheter.

18. The miniaturized pressure sensor module of claim 17, wherein the sensor is coupled to the carrier, such that when the carrier is attached to the catheter, the sensor is electrically isolated from the catheter.

* * * * *

UNITED STATES PATENT AND TRADEMARK OFFICE
CERTIFICATE OF CORRECTION

| | |
|---|---|
| PATENT NO. | : 6,994,695 B1 |
| APPLICATION NO. | : 10/127154 |
| DATED | : February 7, 2006 |
| INVENTOR(S) | : Millar |

Page 1 of 1

It is certified that error appears in the above-identified patent and that said Letters Patent is hereby corrected as shown below:

<u>In the Claims</u>

Col. 10, line 14: Please delete "claim 13" and substitute therefor --claim 15--.

Signed and Sealed this

Twenty-sixth Day of December, 2006

JON W. DUDAS
*Director of the United States Patent and Trademark Office*